United States Patent
Goldberg

(10) Patent No.: US 9,616,040 B2
(45) Date of Patent: Apr. 11, 2017

(54) CITRATE RESORPTION OF BONE AS A TREATMENT FOR SPINAL STENOSIS

(71) Applicant: Joel Steven Goldberg, Hillsborough, NC (US)

(72) Inventor: Joel Steven Goldberg, Hillsborough, NC (US)

(73) Assignee: Joel Steven Goldberg, Hillsborough, NC (US)

( * ) Notice: Subject to any disclaimer, the term of this patent is extended or adjusted under 35 U.S.C. 154(b) by 0 days.

(21) Appl. No.: 14/991,931

(22) Filed: Jan. 9, 2016

(65) Prior Publication Data

US 2016/0158175 A1    Jun. 9, 2016

(51) Int. Cl.
*A61K 31/194* (2006.01)
*A61K 9/00* (2006.01)

(52) U.S. Cl.
CPC .......... *A61K 31/194* (2013.01); *A61K 9/0085* (2013.01)

(58) Field of Classification Search
CPC ............................ A61K 31/194; A61K 9/0085
See application file for complete search history.

(56) References Cited

PUBLICATIONS

Seifter, E., & Lavine, L. S. (1961). Aspects of Citric Acid Chemistry Related to Bone. Bull N YAcad Med, 37(3), 156-166.*
Fritz, J.M. et al, Lumbar spinal stenosis: A review . . . outcome measurements, Arch Phys Med Rehab 79:1998, p. 700-708.
Costandi, S. et al, Lumbar spinal stenosis:Therapeutic options review,Pain Practice 15:2015 p. 68-81.
Hennequin, M. et al, Effect of different pH values of citric acid on the calcium . . . human root dentin, J. Endodontics 20:1994 p. 551-554.
Bhatnagar, R. et al, Decalcifying effects of three chelating agents, J Endodontology 18:2006 p. 43-46.

* cited by examiner

*Primary Examiner* — Sahar Javanmard

(57) ABSTRACT

Spinal stenosis is a common debilitating illness that produces symptoms of neurogenic claudication, radiculopathy and weakness. Present therapies include administration of analgesics, epidural injections of local anesthetic with corticosteroids and decompression laminectomy. In vitro, citrate ion can resorb vertebral cortical bone by chelating calcium without destruction of the ligamentum flavum or dura mater. This non-enzymatic spontaneous chemical reaction occurs at neutral pH, 37° C. and in an isotonic solution and in vitro produces an average cortical bone weight loss of 17% after 168 hours. In this invention epidural infusion of citrate in the form of an isotonic solution of sodium citrate/citric acid buffer at neutral pH will resorb a significant amount of vertebral bone such that the symptoms of spinal stenosis are ameliorated.

1 Claim, 2 Drawing Sheets

CITRATE RESORPTION OF BONE AS A TREATMENT FOR SPINAL STENOSIS

CROSS-REFERENCES TO RELATED APPLICATIONS

None

FEDERALLY FUNDED RESEARCH

Not applicable

BACKGROUND OF THE INVENTION

Spinal stenosis of the lumbar and cervical spine is a common pain condition frequently found in the elderly. (Fritz, Delitto, Welch, & Erhard, 1998) Some of the symptoms of spinal stenosis include neurogenic claudication, extremity weakness, and radiculopathy. Patients predisposed to spinal stenosis include those who were born with congenitally shortened vertebral pedicles or those who have suffered excessive spondylosis of the spine secondary to degenerative disc disease. Spinal stenosis can occur at multiple spinal levels and multiple locations within a particular level including lateral recess, central canal, and intervertebral foraminal stenosis. As the spondylosis increases causing more pressure on the spinal cord or spinal nerves the symptoms progress.

Treatment of spinal stenosis includes administration of analgesics, epidural injections of local anesthetics with corticosteroids and decompression laminectomy. (Costandi, Chopko, Mekhail, Dews, & Mekhail, 2015) Decompression laminectomy is the preferred surgical procedure but includes risks of worsening the pain and nerve or spinal cord injury.

Decalcification of bone by citric acid/formic acid mixtures at low pH is a well-known histologic technique, but decalcification of bone exclusively with citrate under physiologic conditions of pH, tonicity and temperature has not been reported. (Seifter & Lavine, 1961; Vega, Narda, & Ferretti, 2003) Citrate can chelate calcium from calcium phosphate and calcium hydroxyapatite, the two major components of cortical bone. The rate of the reaction can be observed over days and definitely within a week.

Epidural injection for relief of various types of spinal pain including stenosis of the spinal cord, intervertebral foramina and lateral recess is a common low risk procedure performed by many pain practitioners. There are two main methods to perform the injection either transforaminal or translaminar. (Andreisek et al., 2013) Transforaminal injection is felt to especially target the anterior lumbar epidural space. (Manchikanti et al., 2015)

Infusion of substances into the epidural space with implantation of an epidural catheter is a common therapy that provides long term pain relief. Common medications for infusion include opioids, local anesthetics, clonidine and baclofen. (Jones, Anthony, Torda, & Poulos, 1988; Krishnamoorthy, Ravi, & Ganesan, 2015) Catheters with an infusion device can be implanted for years or catheters with an external port are frequently implanted in a patient for one week. Typical infusion rates are 5-15 ml per hour. Some complications of long term implantation of an epidural catheter include migration, bleeding, infection and granuloma formation.

In this invention continuous infusion of citrate via an epidural catheter will resorb bone that is contiguous to the epidural space and alleviate some of the symptoms of spinal stenosis.

DRAWINGS

Figure 1:
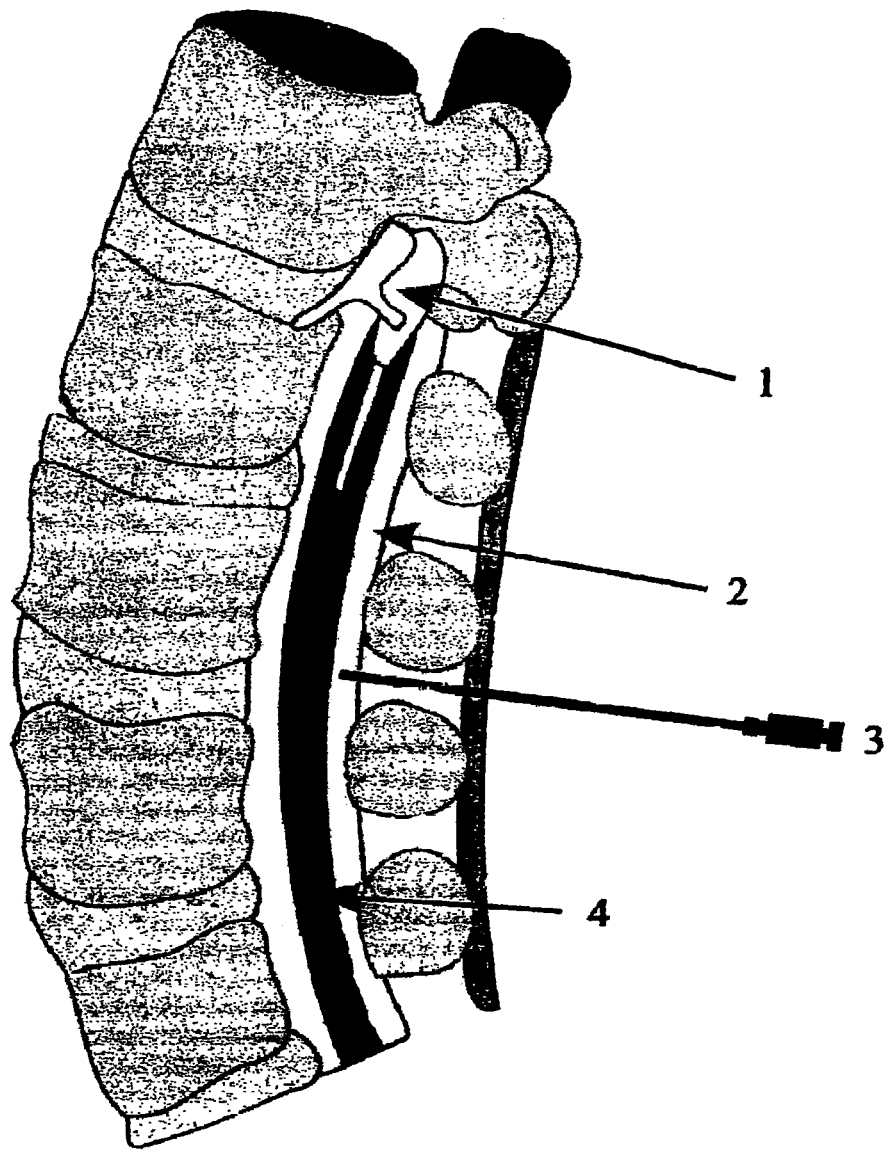

FIG. 1 shows the location of the epidural space and a needle within the epidural space that is required for percutaneous catheterization of the epidural space. Label 1 is the spinal cord, label 2 is the epidural space, label 3 is the epidural needle that guides placement of the epidural catheter and label 4 is the subarachnoid space.

Figure 2:
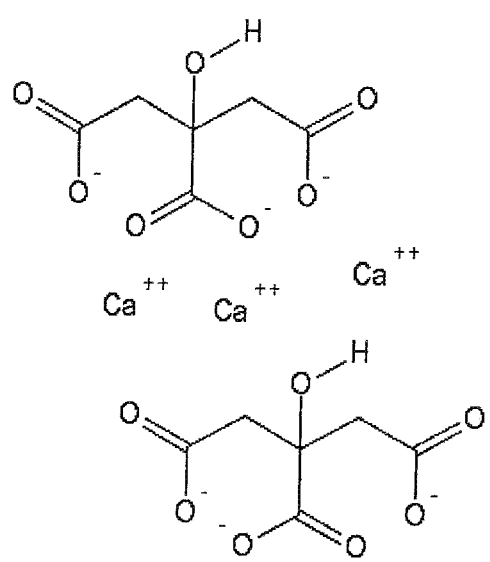

FIG. 2 shows chelation of calcium ion by citrate.

DETAILED DESCRIPTION OF THE INVENTION

Spinal stenosis caused by spondylosis is a common debilitating condition that produces pain, weakness and rarely autonomic dysfunction of the bladder and bowel. An isotonic solution of citrate in the form of sodium citrate or sodium citrate/citric acid buffer can resorb bone at 37° C. at neutral pH. In vitro the chemical reaction is non-enzymatic, spontaneous and occurs at a rate that can be easily observed in one week or less. Infusion of citrate via an epidural catheter will resorb spondylitic bone that produces central, foraminal and/or lateral recess spinal stenosis without disrupting the ligamentum flavum or dura mater.

Insertion of an epidural catheter and subsequent infusion into the epidural space is a common low risk medical procedure. (FIG. 1) This procedure can be performed successfully with or without guided imaging.

In vitro experiments definitively show that bovine vertebral bone resorption occurs spontaneously without a catalyst in an isotonic solution of citrate at 37° C. at neutral pH.

Experimental Section

Methods

Fresh bovine vertebral bone was cut into 1-3 g sections with a diamond saw blade. Non-cortical medullary bone was trimmed from the cortical bone and the sections were dried while incubated for 12 hours at 37° C. and then weighed. Bone sections were then incubated in solutions of citric acid, sodium citrate, sodium citrate/citric acid buffer and Depo-Medrol at 37° C. for 96-168 hours. Bone sections were then dried and reweighed. The isotonic sodium citrate/citric acid buffer was prepared by using a citric acid buffer calculator with buffer strength at 65 mM and pH 7.0. 1.8773 g of sodium citrate and 0.0223 g of citric acid were dissolve in 100 ml of distilled water.

The lamina of a freshly killed deer spine was cut with a diamond saw blade and the spinal cord, ligamentum flavum, and dura mater were dissected from the bone. The spinal cord, ligamentum flavum and dura mater were incubated in an isotonic solution of citrate buffer at pH 7.2 for 12 hours. The specimens were placed on chromatography paper to absorb excess buffer solution, and then weighed and placed back in the incubator for 96 hours and reweighed after excess buffer solution was absorbed on the paper. (Table 7) The dura mater was intact even after 168 hours of immersion in the isotonic citrate/citric acid buffer.

Results

1. Citric acid resorption of bone at 37° C. after 96 hours is pH dependent and not clinically use for epidural infusion because of high acidity. (Table 1)

TABLE 1

Citric acid resorption of bone at 37° C. after 96 hours.

| Molarity | pH | Initial wt. (g) | Final wt. (g) | Wt. change (g) | % change |
|---|---|---|---|---|---|
| 1M | 1.57 | 1.68827 | 1.20200 | −0.48627 | −0.28802 |
| 0.1M | 2.08 | 1.59857 | 1.40701 | −0.19156 | −0.11983 |
| 0.01M | 2.62 | 1.38158 | 1.32030 | −0.06128 | −0.04435 |
| 0.001M | 3.25 | 1.23600 | 1.24032 | +0.00432 | +0.00349 |

2. Sodium citrate resorption of bone after 96 hours. (Table 2)

TABLE 2

Sodium citrate resorption of bone at 37° C. after 96 hours.

| Molarity | pH | Initial wt. (g) | Final wt. (g) | Wt. change (g) | % change |
|---|---|---|---|---|---|
| 1M | 8.67 | 2.60466 | 2.65347 | −0.04881 | −0.01873 |
| 0.1M | 9.27 | 1.42708 | 1.41115 | −0.01593 | −0.01116 |
| 0.01M | 7.78 | 2.40706 | 2.37445 | −0.03261 | −0.01319 |
| 0.001M | 7.65 | 2.06348 | 2.06271 | −0.00077 | −0.00037 |

3. Sodium citrate resorption of bone at 37° C. after 168 hours is greatest at 0.15 M. (Table 3)

TABLE 3

Sodium citrate resorption of bone at 37° C. after 168 days.

| Molarity | pH | Initial wt. (g) | Final wt. (g) | Wt. change (g) | % change |
|---|---|---|---|---|---|
| 1M | 8.67 | 3.41315 | 3.45458 | +0.04143 | +0.01213 |
| 1M | 8.67 | 1.33843 | 1.33480 | −0.00363 | −0.00305 |
| 0.55M | 8.68 | 3.57904 | 3.55390 | −0.02514 | −0.00196 |
| 0.55M | 8.68 | 1.18835 | 1.16223 | −0.02612 | −0.01386 |
| 0.25M | 9.12 | 2.35946 | 2.35042 | −0.00904 | −0.00373 |
| 0.25M | 9.12 | 1.41114 | 1.39456 | −0.01658 | −0.01174 |
| 0.15M | 9.16 | 2.42250 | 2.30963 | −0.11287 | −0.04659 |
| 0.15M | 9.16 | 1.33035 | 1.25379 | −0.07656 | −0.05754 |
| 0.125M | 9.20 | 2.45241 | 2.44973 | −0.00268 | −0.00109 |
| 0.125M | 9.20 | 1.40900 | 1.35555 | −0.05345 | −0.03799 |
| 0.1M | 9.27 | 2.53647 | 2.45633 | −0.08014 | −0.03159 |
| 0.1M | 9.27 | 1.86700 | 1.85671 | −0.01029 | −0.00551 |

4. Sodium citrate/citric acid buffer resorption of bone at 37° C. after 96 hours shows maximum bone resorption at 0.1M. (Table 4)

TABLE 4

Sodium citrate/citric acid buffer resorption of bone after 96 hours at 37° C.

| Molarity | pH | Initial wt. (g) | Final wt. (g) | Wt. change (g) | % change |
|---|---|---|---|---|---|
| 0.1M | 6.18 | 2.33108 | 2.24740 | −0.08368 | −0.03589 |
| 0.01M | 6.35 | 2.49800 | 2.43884 | −0.05916 | −0.02368 |
| 0.001M | 6.68 | 1.90300 | 1.85830 | −0.04476 | −0.02348 |
| 0.0001M | 6.92 | 1.43822 | 1.40780 | −0.03042 | −0.02115 |

5. Isotonic sodium citrate/citric acid buffer (pH 7.29) shows greater than 17% resorption at 37° C. after 168 hours. (Table 5)

TABLE 5

Isotonic sodium citrate/citric acid buffer resorption of bone at 37° C. after 168 hours.

| Osmolarity (mOsm/L) | pH | Initial wt. (g) | Final wt. (g) | Wt. change (g) | % change |
|---|---|---|---|---|---|
| 295 | 7.29 | 1.18014 | 0.97763 | −0.20251 | −0.17159 |
| 295 | 7.29 | 1.21427 | 1.10342 | −0.11085 | −0.09128 |
| 295 | 7.29 | 1.44123 | 1.30382 | −0.13741 | −0.09534 |
| 295 | 7.29 | 2.32611 | 2.00717 | −0.31894 | −0.13711 |
| 295 | 7.29 | 1.45600 | 1.20506 | −0.25094 | −0.17234 |
| 295 | 7.29 | 2.43418 | 2.20900 | −0.22518 | −0.09250 |
| 295 | 7.29 | 1.39309 | 1.10700 | −0.28609 | −0.20536 |
| 295 | 7.29 | 3.74126 | 3.40043 | −0.34083 | −0.09110 |
| 295 | 7.29 | 1.42788 | 1.20100 | −0.22688 | −0.15889 |
| 295 | 7.29 | 1.71945 | 1.50100 | −0.21845 | −0.12704 |
| 295 | 7.29 | 0.96185 | 0.70843 | −0.25342 | −0.26347 |
| 295 | 7.29 | 1.14490 | 0.80118 | −0.34372 | −0.30021 |
| Average (n = 12) | | | | | −17.53% |

6. Depo-Medrol resorption of bone at 37° C., (pH 6.50) after 168 hours. (Table 6)

TABLE 6

Depo-Medrol resorption of bone at 37° C. after 168 hours.

| pH | Initial wt. (g) | Final wt. (g) | Wt. change (g) | % change |
|---|---|---|---|---|
| 6.50 | 2.66761 | 2.58570 | −0.08191 | −0.03070 |
| 6.50 | 2.58671 | 2.55650 | −0.03021 | −0.01167 |
| 6.50 | 2.03385 | 2.00113 | −0.03272 | −0.01608 |

7. Changes in weight of ligamentum flavum, dura mater and spinal cord sections in isotonic citrate buffer (pH 7.20) at 37° C. after 96 hours.

TABLE 7

Weight changes of ligamentum flavum, dura mater and spinal cord in isotonic citrate buffer.

| | Osmolarity (mOsm/L) | pH | Initial wt. (g) | Final wt. (g) | % change |
|---|---|---|---|---|---|
| Ligamentum flavum | 295 | 7.20 | 0.94901 | 0.94807 | −0.00099 |
| Dura mater | 295 | 7.20 | 0.31009 | 0.33459 | +0.07900 |
| Spinal cord | 295 | 7.20 | 7.68486 | 7.80410 | +0.01551 |

Discussion

In cortical bone, citrate chelates calcium within calcium phosphate and calcium hydroxyapatite. (FIG. 2) This chemical reaction is spontaneous, non-enzymatic and occurs at physiologic pH in an isotonic solution. The $K_{sp}$ for calcium phosphate is $2.53 \times 10^{-33}$ and for calcium hydroxyapatite is $6.8 \times 10^{-37}$. Although both substances are very insoluble, this invention shows that the crystal matrix of calcium hydroxyapatite and calcium phosphate can be broken apart by citrate without addition of a catalyst or heat under physiologic conditions. The mechanism for chelation of calcium is such that once initiated, the reaction is driven toward resorption of calcium from the phosphate or hydroxyapatite. With benefits from the uncommon ion effect, chelation acts as a sink for calcium ions shifting the chemical equilibrium in favor of resorption of bone.

Toxicity

Citrate administered in large quantities is non-toxic. In an animal model approximately 30% of citrate administered intravenously is metabolized in the liver to bicarbonate and carbon dioxide. (Curtin & King, 1955) Examples of medications that are not neurotoxic and approved by the FDA for epidural administration are listed in Table 8. In the preferred embodiment of this invention, administration of an isotonic solution of sodium citrate/citric acid buffer at pH 7.2 into the epidural space is unlikely to cause neurotoxicity.

FDA approved epidural medications. (Table 8)

TABLE 8

FDA approved epidural medications.

| Medication proprietary | Medication generic | pH | Approximate osmolarity (mOsm/L) |
|---|---|---|---|
| Lioresal | Baclofen | 5.0-7.0 | 308 |
| Duraclon | Clonidine HCl | 5.0-7.0 | 308 |
| Duramorph | Morphine $SO_4$ | 2.5-6.5 | 308 |
| Marcaine | Bupivicaine | 4.0-6.5 | 290 |
| Nesacaine-MPF3% | 2-Chloroprocaine HCl (no preservative) | 2.7-4.0 | |

Benefits to Society

Citrate resorption of bone by chelation of calcium may change the present therapies for the treatment of spinal stenosis. Beyond the treatment of spinal stenosis, chelation of calcium by citrate may be useful for the resorption of calcium from arthritic joints or early atherosclerotic plaques.

REFERENCES

Andreisek, G., Jenni, M., Klingler, D., Wertli, M., Elliott, M., Ulbrich, E. J., et al. (2013). Access routes and reported decision criteria for lumbar epidural drug injections: a systematic literature review. *Skeletal Radiol*, 42(12), 1683-1692.

Costandi, S., Chopko, B., Mekhail, M., Dews, T., & Mekhail, N. (2015). Lumbar spinal stenosis: therapeutic options review. *Pain Pract*, 15(1), 68-81.

Curtin, C. O., & King, C. G. (1955). The metabolism of ascorbic acid-1-C14 and oxalic acid-C14 in the rat. *J Biol Chem*, 216(2), 539-548.

Fritz, J. M., Delitto, A., Welch, W. C., & Erhard, R. E. (1998). Lumbar spinal stenosis: a review of current concepts in evaluation, management, and outcome measurements. *Arch Phys Med Rehabil*, 79(6), 700-708.

Jones, R. F., Anthony, M., Torda, T. A., & Poulos, C. (1988). Epidural baclofen for intractable spasticity. *Lancet*, 1(8584), 527.

Krishnamoorthy, K., Ravi, S., & Ganesan, I. (2015). Evaluation of Efficacy of Epidural Clonidine with 0.5% Bupivacaine for Postoperative Analgesia for Orthopaedic Lower Limb Surgeries. *J Clin Diagn Res*, 9 (9), UC14-18.

Manchikanti, L., Kaye, A. D., Manchikanti, K., Boswell, M., Pampati, V., & Hirsch, J. (2015). Efficacy of epidural injections in the treatment of lumbar central spinal stenosis: a systematic review. *Anesth Pain Med*, 5 (1), e23139.

Seifter, E., & Lavine, L. S. (1961). Aspects of Citric Acid Chemistry Related to Bone. *Bull N Y Acad Med*, 37(3), 156-166.

Vega, E. D., Narda, G. E., & Ferretti, F. H. (2003). Adsorption of citric acid from dilute aqueous solutions by hydroxyapatite. *J Colloid Interface Sci*, 268(1), 37-42.

Having described my invention, I claim:

1. A method to treat the symptoms of spinal stenosis in a mammal by administration of a solution of citrate through an epidural catheter, wherein the solution of citrate is comprised of sodium citrate and citric acid at pH 6.0-8.0 with a tonicity between 280-310 milliosmoles per liter and continuously administered at an infusion rate of 5 to 15 milliliters per hour for 96 to 168 hours.

* * * * *